US012605493B2

(12) United States Patent
Ericson et al.

(10) Patent No.: US 12,605,493 B2
(45) Date of Patent: Apr. 21, 2026

(54) DIALYSIS SYSTEM HAVING LOW VOLUME PERITONEAL DIALYSIS PATIENT FILL TEMPERATURE CONTROL

(71) Applicants: Vantive US Healthcare LLC, Deerfield, IL (US); Vantive Health GMBH, Glattpark (CH)

(72) Inventors: Bjorn Ericson, Lund (SE); Oskar Erik Frode Styrbjorn Fallman, Lund (SE)

(73) Assignees: Vantive US Healthcare LLC, Deerfield, IL (US); Vantive Health GmbH, Glattpark (CH)

( * ) Notice: Subject to any disclaimer, the term of this patent is extended or adjusted under 35 U.S.C. 154(b) by 280 days.

(21) Appl. No.: 18/215,269

(22) Filed: Jun. 28, 2023

(65) Prior Publication Data

US 2023/0414853 A1      Dec. 28, 2023

Related U.S. Application Data

(60) Provisional application No. 63/356,328, filed on Jun. 28, 2022.

(51) Int. Cl.
A61M 1/28 (2006.01)
(52) U.S. Cl.
CPC ............ A61M 1/282 (2014.02); A61M 1/284 (2014.02); A61M 1/287 (2013.01); *A61M 2205/3337* (2013.01); *A61M 2205/3372* (2013.01); *A61M 2205/50* (2013.01); *A61M 2205/7509* (2013.01); *A61M 2205/7518* (2013.01)

(58) Field of Classification Search
CPC ...... A61M 1/282; A61M 1/284; A61M 1/287; A61M 2205/3337; A61M 2205/3372; A61M 2205/50; A61M 2205/7509; A61M 2205/7518
See application file for complete search history.

(56) References Cited

U.S. PATENT DOCUMENTS

2022/0203008 A1* 6/2022 Jansson ............... A61M 1/1688

* cited by examiner

*Primary Examiner* — John Kim
(74) *Attorney, Agent, or Firm* — K&L Gates LLP

(57) ABSTRACT

A peritoneal dialysis ("PD") system includes a PD fluid pump, a dual lumen patient line including fresh and used PD fluid lumens, a filter set in fluid communication with the fresh and used PD fluid lumens, a valve provided either with a patient's transfer set or with the filter set, and a control unit configured, after a patient drain, to (i) prompt a patient or caregiver to close the valve when the valve is a manual valve, or (ii) cause the valve to close automatically when the valve is an electrically or pneumatically controlled valve. The control unit is further configured to cause the PD fluid pump, with the valve closed, to pump fresh, heated PD fluid into the fresh PD fluid lumen to displace unheated PD fluid from the fresh PD fluid lumen, through the filter set, into the used PD fluid lumen. A corresponding method is also disclosed.

15 Claims, 3 Drawing Sheets

DIALYSIS SYSTEM HAVING LOW VOLUME PERITONEAL DIALYSIS PATIENT FILL TEMPERATURE CONTROL

PRIORITY CLAIM

This application claims priority to and the benefit as a non-provisional application of U.S. Provisional Patent Application No. 63/356,328, filed on Jun. 28, 2022, the entire contents of which are hereby incorporated by reference and relied upon.

TECHNICAL FIELD

The present disclosure relates generally to medical fluid treatments, and in particular to dialysis fluid treatments that require fluid heating.

BACKGROUND

Due to various causes, a person's renal system can fail. Renal failure produces several physiological derangements. For instance, it is no longer possible to balance water and minerals or to excrete daily metabolic load. Additionally, toxic end products of metabolism, such as urea, creatinine, uric acid, and others, may accumulate in a patient's blood and tissue.

Reduced kidney function and, above all, kidney failure is treated with dialysis. Dialysis removes waste, toxins, and excess water from the body that normal functioning kidneys would otherwise remove. Dialysis treatment for the replacement of kidney functions is critical to many people because the treatment is lifesaving.

One type of kidney failure therapy is Hemodialysis ("HD"), which in general uses diffusion to remove waste products from a patient's blood. A diffusive gradient occurs across a semi-permeable dialyzer between the blood and an electrolyte solution, called dialysate or dialysis fluid, to cause diffusion.

Hemofiltration ("HF") is an alternative renal replacement therapy that relies on a convective transport of toxins from a patient's blood. HF is accomplished by adding substitution or replacement fluid to an extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, where the transfer of waste, toxins, and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins, and excess water to take place. The source may include multiple liters of dialysis fluid including several solution bags.

The PD machines pump used or spent dialysate from the patient's peritoneal cavity, though the catheter, to drain. As with the manual process, several drain, fill, and dwell cycles occur during dialysis. A "last fill" may occur at the end of an APD treatment. The last fill fluid may remain in the peritoneal chamber of the patient until the start of the next treatment, or may be manually emptied at some point during the day.

The PD machines also heat the PD fluid to body temperature, e.g., 37° C., prior to delivery to the patient's peritoneal cavity. The patient line extending from the PD machine to the patient's transfer set (leading to an indwelling PD catheter) remains full of fluid, typically patient effluent, during a patient dwell phase, which can last multiple hours. The fluid in patient line cools to room temperature over the patient dwell and is returned to the patient's peritoneal cavity unheated at the beginning of the next patient fill. For most patients, the small amount of unheated fluid is not an issue. But for low volume patients, such as pediatric patients, even a small amount of unheated fluid delivered to the peritoneal cavity can be uncomfortable at the least.

An improved way to deliver PD fluid to a low volume PD patient is accordingly needed.

SUMMARY

The present disclosure sets forth an automated peritoneal dialysis ("PD") system, which improves PD fluid filling for low volume PD patients, such as pediatric patients. The system includes a PD machine or cycler. The PD machine is configured to deliver fresh, heated PD fluid to a patient at, for example, 14 kPa (2.0 psig) or higher. The PD machine is capable of removing used PD fluid or effluent from the patient at, for example, −9 kPa (−1.3 psig) or higher. Fresh PD fluid is delivered via a dual lumen patient line to the patient and is first heated to a body fluid temperature, e.g., 37° C. The heated PD fluid is then pumped through a fresh PD fluid lumen of the dual lumen patient line to a disposable filter set. The disposable filter set communicates fluidly with the fresh and used PD fluid lumens of the dual lumen patient line, which is heat disinfected and reusable in one embodiment. The disposable filter set includes a sterilizing grade filter membrane that further filters fresh PD fluid. The disposable filter set is provided in one embodiment as a last chance filter for the PD machine, which has been heat disinfected between treatments. Any pathogens that may remain after disinfection, albeit unlikely, are filtered from the PD fluid via the sterilizing grade filter membrane.

During a subsequent patient dwell, fresh PD fluid remaining in the fresh PD fluid lumen cools from a body temperature to roughly ambient temperature. For low fill volume patients, initially filling the patient with cooler PD fluid may lead to patient discomfort at the least. It is accordingly contemplated that at the end of each patient drain for which there is a subsequent patient fill, to cause the user interface of the PD system and machine of the present disclosure to prompt the patient or caregiver to close a manual valve, which may be provided with the patient's transfer set or with the disposable filter set. The manual valve, when closed, causes the unheated fluid in the fresh PD fluid lumen to be flushed from the fresh PD fluid lumen into the used PD fluid lumen. Notably, the patient drain may end when (i) the PD machine records that a prescribed amount of used PD fluid or effluent has been removed from the patient, (ii) upon a control unit of the PD machine determining a low patient drain flowrate indicating that the patient is empty or almost empty, or (iii) or upon the control unit determining an increased patient drain pressure, which again indicates that the patient is empty or almost empty. At the end of the patient drain as determined by any one or more of (i) to (iii), the user interface audibly, visually, or audiovisually prompts the patient or caregiver to close the manual valve.

After the prompt to close the manual valve, the user interface may display a confirm button, which the patient or caregiver presses to confirm that the manual valve has been closed. At the same time, or after the confirm button has been pressed, the control unit in one embodiment causes a PD fluid pump, with the appropriate PD machine valves open, to run a pressure test by attempting to pump PD fluid, e.g., a small amount such as five milliliters ("ml"), towards the patient. If the manual valve has been properly closed, a PD machine pressure sensor detects a quick rise in positive pressure of the closed line. If the manual valve has not been properly closed, the pressure sensor will not detect the characteristic or expected quick rise in positive pressure. In response, the control unit is configured to again cause the user interface to audibly, visually, or audiovisually prompt the patient or caregiver to close the manual valve. The above procedure is repeated until the control unit confirms that the manual valve has been closed.

After it is confirmed that the manual valve has been closed, the control unit causes the appropriate PD machine valves to be opened so that heated PD fluid can be delivered to the disposable filter set, pushing the unheated PD fluid into the used PD fluid lumen, towards machine drain. The control unit causes the PD fluid pump to pump at least a fresh PD fluid lumen volume's worth of fresh, heated PD fluid (e.g., 30 to 50 ml) into the fresh PD fluid lumen of the dual lumen patient line, e.g., a reusable dual lumen patient line. A corresponding volume of unheated, room temperature PD fluid is displaced from the fresh PD fluid lumen into the used PD fluid lumen via the disposable filter set. A similar corresponding volume of unheated, room temperature used PD fluid or effluent is displaced from the used PD fluid lumen, into lines or tubes within the PD machine, thereby pushing the used PD fluid towards a drain line connected to the PD machine.

After the fresh PD fluid lumen volume's worth of fresh, heated PD fluid (e.g., 30 to 50 ml) is pumped by the PD fluid pump so as to fill the fresh PD fluid lumen, the control unit, via the user interface, prompts the patient or caregiver to the open the manual valve located either at the patient's transfer set or at a connector of the disposable filter set. After the prompt to open the manual valve is provided by the user interface, the user interface may again display a confirm button, which the patient or caregiver presses to confirm that the manual valve has been opened. After the confirm button has been pressed, the control unit causes the PD fluid pump, with the appropriate PD machine valves open, to pump the patient's prescribed fill volume of fresh, heated PD fluid into the peritoneal cavity of the patient. The above process is repeated for each low volume patient fill.

In an alternative and in one preferred embodiment, after the prompt to open the manual valve is provided by the user interface, the control unit may perform a pressure test to determine if the manual valve has been opened. The pressure test may be performed by causing a small amount of fluid, such as five milliliters ("ml"), to be pumped towards the manual valve. If the manual valve has been properly opened, the relevant pressure sensor will not measure a significant pressure rise, after which the patient's prescribed fill volume of fresh, heated PD fluid is pumped into the peritoneal cavity of the patient. In a further alternative embodiment, the control unit confirms the opening of the manual valve via a pressure test in which the PD fluid pump applies a small amount of pressure, positive or negative, at the manual valve before instructing a user to open the valve. When the manual valve has been properly opened, the relevant pressure sensor measures a significant pressure increase or decrease, after which the patient's prescribed fill volume of fresh, heated PD fluid may be pumped into the peritoneal cavity of the patient.

In light of the disclosure set forth herein, and without limiting the disclosure in any way, in a first aspect of the present disclosure, which may be combined with any other aspect, or portion thereof, a peritoneal dialysis ("PD") system includes a housing, a PD fluid pump housed by the housing, a dual lumen patient line extending from the housing, the dual lumen patient line including a fresh PD fluid lumen and a used PD fluid lumen, a filter set in fluid communication with the fresh PD fluid lumen and the used PD fluid lumen of the dual lumen patient line, a valve provided either with a patient's transfer set or with the filter set, the valve positioned such that when closed, PD fluid is forced from the fresh PD fluid lumen into the used PD fluid lumen, and a control unit, the PD fluid pump under control of the control unit. The control unit is configured after a patient drain to (i) prompt a patient or caregiver to close the valve when the valve is a manual valve or (ii) cause the valve to close automatically when the valve is an electrically or pneumatically controlled valve. The control unit is further configured such that upon the closing of the valve, the PD fluid pump is caused to pump fresh, heated PD fluid into the fresh PD fluid lumen to displace unheated PD fluid from the fresh PD fluid lumen, through the filter set, into the used PD fluid lumen.

In a second aspect of the present disclosure, which may be combined with any other aspect, or portion thereof, the filter set includes a sterilizing grade filter membrane, wherein the displaced unheated PD fluid is displaced through the sterilizing grade filter membrane into the used PD fluid lumen.

In a third aspect of the present disclosure, which may be combined with any other aspect, or portion thereof, the manual valve is a manual ball, twist, gate, or needle valve.

In a fourth aspect of the present disclosure, which may be combined with any other aspect, or portion thereof, the PD system further incudes a pressure sensor. The control unit is further configured to cause the PD fluid pump to attempt to pump a test amount of fresh PD fluid towards the fresh PD fluid lumen and to monitor an output from the pressure sensor to determine if the valve is closed.

In a fifth aspect of the present disclosure, which may be combined with any other aspect, or portion thereof, the control unit is further configured to monitor the output from the pressure sensor to determine if the valve is closed prior to causing the PD fluid pump to pump fresh, heated PD fluid into the fresh PD fluid lumen to displace unheated PD fluid from the fresh PD fluid lumen, through the filter set, into the used PD fluid lumen.

In a sixth aspect of the present disclosure, which may be combined with any other aspect, or portion thereof, the control unit is further configured to monitor the output from the pressure sensor after the patient or caregiver confirms that the manual valve has been closed.

In a seventh aspect of the present disclosure, which may be combined with any other aspect, or portion thereof, prompting the patient or caregiver to close the valve, when the valve is the manual valve, includes providing a confirm button for the patient or caregiver to press after closing the manual valve.

In an eighth aspect of the present disclosure, which may be combined with any other aspect, or portion thereof, the control unit is further configured, such that after the PD fluid pump is caused to pump fresh, heated PD fluid into the fresh PD fluid lumen, (iii) to cause the patient or caregiver to be prompted to open the valve when the valve is the manual valve, or (iv) to cause the valve to be opened automatically when the valve is the electrically or pneumatically controlled valve.

In a ninth aspect of the present disclosure, which may be combined with any other aspect, or portion thereof, prompting the patient or caregiver to open the valve when the valve is the manual valve includes providing a confirm button for the patient or caregiver to press after opening the manual valve.

In a tenth aspect of the present disclosure, which may be combined with any other aspect, or portion thereof, the control unit is further configured to cause the PD fluid pump to pump a prescribed fill volume of fresh, heated PD fluid to the patient after the valve is opened.

In an eleventh aspect of the present disclosure, which may be combined with any other aspect, or portion thereof, a peritoneal dialysis ("PD") system includes a housing, a PD fluid pump housed by the housing, a dual lumen patient line extending from the housing, the dual lumen patient line including a fresh PD fluid lumen and a used PD fluid lumen, a valve provided with a patient's transfer set, the valve positioned such that when closed, PD fluid is forced from the fresh PD fluid lumen into the used PD fluid lumen, and a control unit, the PD fluid pump under control of the control unit. The control unit is configured after a patient drain to (i) prompt a patient or caregiver to close the valve when the valve is a manual valve, or (ii) cause the valve to close automatically when the valve is an electrically or pneumatically controlled valve. The control unit is further configured such that after the closing of the valve, the PD fluid pump is caused to pump fresh, heated PD fluid into the fresh PD fluid lumen to displace unheated PD fluid from the fresh PD fluid lumen into the used PD fluid lumen.

In a twelfth aspect of the present disclosure, which may be combined with any other aspect, or portion thereof, a peritoneal dialysis ("PD") system includes a housing, a PD fluid pump housed by the housing, a patient line extending from the housing, a filter set in fluid communication with the patient line, a valve provided either with a patient's transfer set or with the filter set, the valve positioned such that when closed, PD fluid is removed from the patient line, and a control unit, the PD fluid pump under control of the control unit. The control unit is configured after a patient drain to (i) prompt a patient or caregiver to close the valve when the valve is a manual valve, or (ii) cause the valve to close automatically when the valve is an electrically or pneumatically controlled valve. The control unit is further configured such that after the closing of the valve, the PD fluid pump is caused to pump fresh, heated PD fluid into the patient line.

In a thirteenth aspect of the present disclosure, which may be combined with any other aspect, or portion thereof, PD fluid is removed from the patient line to drain and is backfilled with filtered air.

In a fourteenth aspect of the present disclosure, which may be combined with any other aspect, or portion thereof, a peritoneal dialysis ("PD") system includes a housing, a PD fluid pump housed by the housing, a patient line extending from the housing, a valve provided with a patient's transfer set, the valve positioned such that when closed, PD fluid is removed from the patient line, and a control unit, the PD fluid pump under control of the control unit. The control unit is configured after a patient drain to (i) prompt a patient or caregiver to close the valve when the valve is a manual valve, or (ii) cause the valve to close automatically when the valve is an electrically or pneumatically controlled valve. The control unit is further configured such that after the closing of the valve, the PD fluid pump is caused to pump fresh, heated PD fluid into the patient line.

In a fifteenth aspect of the present disclosure, which may be combined with any other aspect, or portion thereof, a peritoneal dialysis ("PD") method includes determining that a prescribed patient fill is a low volume patient fill, wherein the patient fill takes places via a fresh PD fluid lumen of a dual lumen patient line operating with a PD machine, the dual lumen patient line also including a used PD fluid lumen. The method also includes after determining the low volume patient fill, entering a low volume mode in which prior to the low volume patient fill a valve is closed, the closed valve positioned such that the PD machine is able to displace cooled PD fluid residing in the fresh PD fluid lumen into the used PD fluid lumen by filling the fresh PD fluid lumen with fresh, heated PD fluid.

In a sixteenth aspect of the present disclosure, which may be combined with any other aspect, or portion thereof, the PD method includes the PD machine performing the prescribed patient fill without the cooled PD fluid residing in the fresh PD fluid lumen being displaced when it is determined that the prescribed patient fill is not a low volume patient fill.

In a seventeenth aspect of the present disclosure, which may be combined with any other aspect, or portion thereof, the PD method includes opening the valve so as to enable the PD machine to perform the low volume patient fill after the cooled PD fluid residing in the fresh PD fluid lumen is displaced into the used PD fluid lumen.

In an eighteenth aspect of the present disclosure, which may be combined with any other aspect, or portion thereof, closing and opening the valve includes manually closing and opening the valve.

In a nineteenth aspect of the present disclosure, which may be combined with any other aspect, or portion thereof, closing and opening the valve includes prompting a patient or caregiver to close and open the valve.

In a twentieth aspect of the present disclosure, which may be combined with any other aspect, or portion thereof, the PD method includes confirming that the valve is closed as a condition needed for displacing the cooled PD fluid into the used PD fluid lumen.

In a twenty-first aspect of the present disclosure, which may be combined with any other aspect, or portion thereof, confirming is via a button press at the PD machine.

In a twenty-second aspect of the present disclosure, which may be combined with any other aspect, or portion thereof, the PD method includes confirming that the valve is closed by performing a pressure check on the fresh PD fluid lumen as a condition needed for displacing the cooled PD fluid into the used PD fluid lumen.

In a twenty-third aspect of the present disclosure, which may be combined with any other aspect, or portion thereof, the PD method includes allowing a patient or caregiver to override or disable the low volume mode such that the PD machine may perform the low volume fill without the cooled PD fluid residing in the fresh PD fluid lumen being displaced.

In a twenty-fourth aspect of the present disclosure, which may be combined with any other aspect, or portion thereof, any of the features, functionality and alternatives described in connection with any one or more of FIGS. 1 to 3 may be combined with any of the features, functionality and alternatives described in connection with any other of FIGS. to 3.

In light of the above aspects and present disclosure set forth herein, it is an advantage of the present disclosure to provide an improved system and method for delivering PD fluid to a low volume PD patient.

It is another advantage of the present disclosure to provide a PD fluid system that delivers PD fluid to a PD patient at a body temperature, e.g., 37° C.

It is a further advantage of the present disclosure to provide a PD fluid system that removes effluent from the patient line prior to filling the patient.

Moreover, it is an advantage of the present disclosure to provide a PD fluid system that automatically reconfigures itself to heat the PD fluid prior to patient delivery when the system learns that the fill volume is a low fill volume.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
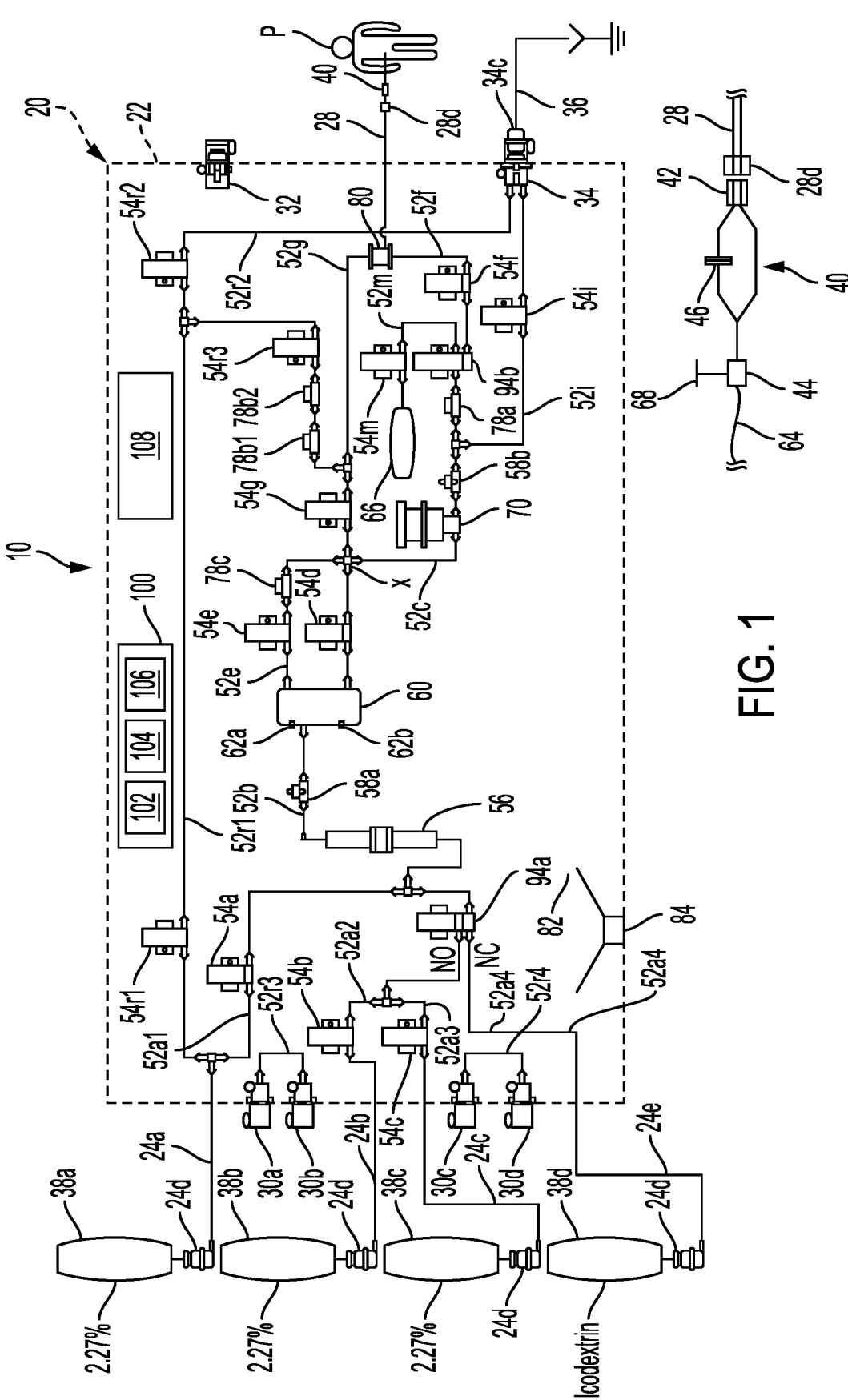
FIG. 1 is a fluid flow schematic of one embodiment for a medical fluid, e.g., PD fluid, system having the low patient fill volume structure and methodology of the present disclosure.

Referring now to the drawings and in particular to FIG. 1, the low volume patient fill structure and methodology of the present disclosure is illustrated via a peritoneal dialysis ("PD") system 10. The example system 10 includes a PD machine or cycler 20 and a control unit 100 having one or more processor 102, one or more memory 104, video controller 106, and user interface 108. The example user interface 108 may alternatively or additionally be a remote user interface, e.g., via a tablet or smartphone. The control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. The control unit 100 in an embodiment controls all electrical, fluid flow, and heating components of the system 10 and receives outputs from sensors of the system 10. System 10 in the illustrated embodiment includes durable and reusable components that contact fresh and used PD fluid, which necessitates that the PD machine or cycler 20 be disinfected between treatments, e.g., via heat disinfection.

System 10 in FIG. 1 includes an inline resistive heater 56, reusable supply lines or tubes 52a1 to 52a4 and 52b, air trap 60 operating with respective upper and lower level sensors 62a and 62b, air trap valve 54d, vent valve 54e located along vent line 52e, reusable line or tubing 52c, PD fluid pump 70, temperature sensors 58a and 58b, pressure sensors 78a, 78b1, 78b2 and 78c, reusable patient tubing or lines 52f and 52g having respective valves 54f and 54g, dual lumen reusable patient line 28, a hose reel 80 for retracting patient line 28, reusable drain tubing or line 52i extending to drain line connector 34 and having a drain line valve 54i, and reusable recirculation disinfection tubing or lines 52r1 and 52r2 operating with respective disinfection valves 54r1 and 54r2. A third recirculation or disinfection tubing or line 52r3 extends between disinfection connectors 30a and 30b for use during disinfection. A fourth recirculation or disinfection tubing or line 52r4 extends between disinfection connectors 30c and 30d for use during disinfection.

System 10 further includes PD fluid containers or bags 38a to 38c (e.g., holding the same or different formulations of PD fluid), which connect to distal ends 24d of reusable PD fluid lines 24a to 24c, respectively. System 10d further includes a fourth PD fluid container or bag 38d that connects to a distal end 24d of reusable PD fluid line 24e. Fourth PD fluid container or bag 38d may hold the same or different type (e.g., icodextrin) of PD fluid than provided in PD fluid containers or bags 38a to 38c. Reusable PD fluid lines 24a to 24c and 24e extend in one embodiment through apertures (not illustrated) defined or provided by the housing 22 of the cycler 20.

System 10 in the illustrated embodiment includes four disinfection connectors 30a to 30d for connecting to distal ends 24d of reusable PD fluid lines 24a to 24c and 24e, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28d of dual lumen reusable patient line 28 into the other PD fluid lumen. Reusable supply tubing or lines 52a1 to 52a4 communicate with reusable supply lines 24a to 24c and 24e, respectively. Reusable supply tubing or lines 52a1 to 52a3 operate with valves 54a to 54c, respectively, to allow PD fluid from a desired PD fluid container or bag 38a to 38c to be pulled into cycler 20. Three-way valve 94a in the illustrated example allows for control unit 100 to select between (i) 2.27% (or other) glucose dialysis fluid from container or bag 38b or 38c and (ii) icodextrin from container or bag 38d. In the illustrated embodiment, icodextrin from container or bag 38d is connected to the normally closed port of three-way valve 94a.

System 10 is constructed in one embodiment such that drain line 52i during a patient fill is fluidly connected downstream from PD fluid pump 70. In this manner, if drain valve 54i fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34c to form a closed disinfection loop. PD fluid pump 70 may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of cycler 20 and a corresponding leak detection sensor 84 outputting to control unit 100. In the illustrated example, system 10 is provided with an additional pressure sensor 78c located upstream of PD fluid pump 70, which allows for the measurement of the suction pressure of pump 70 to help control unit 100 more accurately determine pump volume. Additional pressure sensor 78c in the illustrated embodiment is located along vent line 52e, which may be filled with air or a mixture of air and PD fluid, but which should nevertheless be at the same negative pressure as PD fluid located within PD fluid line 52c.

System 10 in the example of FIG. 1 includes redundant pressure sensors 78b1 and 78b2, the output of one of which is used for pump control, as discussed herein, while the output of the other pressure sensor is a safety or watchdog output to make sure the control pressure sensor is reading accurately. Pressure sensors 78b1 and 78b2 are located along a line including a third recirculation valve 54r3. In still a further example, system 10 may employ one or more cross, marked via an X in FIG. 1, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 94b via a citric acid valve 54m located along a citric acid line 52m. Citric acid line 52m is connected in one embodiment to the normally closed port of second three-way valve 94b, so as to provide redundant valves between citric acid container or bag 66 and the PD fluid circuit during treatment. The redundant valves ensure that no citric (or other) acid reaches the treatment fluid lines during treatment. Citric (or other) acid is instead used during disinfection.

Control unit 100 in an embodiment uses feedback from any one or more of pressure sensors 78a to 78c to enable PD machine 20 to deliver fresh, heated PD fluid to the patient at, for example, 14 kPa (2.0 psig) or higher. The pressure feedback is used to enable PD machine 20 to remove used PD fluid or effluent from the patient at, for example, −9 kPa (−1.3 psig) or higher. The pressure feedback may be used in a proportional, integral, derivative ("PID") pressure routine for pumping fresh and used PD fluid at a desired positive or negative pressure.

Inline resistive heater 56 under control of control unit 100 is capable of heating fresh PD fluid to body temperature, e.g., 37° C., for delivery to patient P at a desired flowrate. Control unit 100 in an embodiment uses feedback from temperature sensor 58a in a PID temperature routine for pumping fresh PD fluid to patient P at a desired temperature.

FIG. 1 also illustrates that system 10 includes and uses a disposable filter set 40, which communicates fluidly with the fresh and used PD fluid lumens of dual lumen reusable patient line 28. Disposable filter set 40 includes a disposable connector 42 that connects to a distal end 28d of reusable patient line 28. Disposable filter set 40 also includes a connector 44 that connects to the patient's transfer set. Disposable filter set 40 further includes a sterilizing grade filter membrane 46 that further filters fresh PD fluid. Disposable filter set 40 is provided in one embodiment as a last chance filter for the PD machine 20, which has been heat disinfected between treatments. Any pathogens that may remain after disinfection, albeit unlikely, are filtered from the PD fluid via the sterilizing grade filter membrane 46 of disposable filter set 40.

Figure 2:
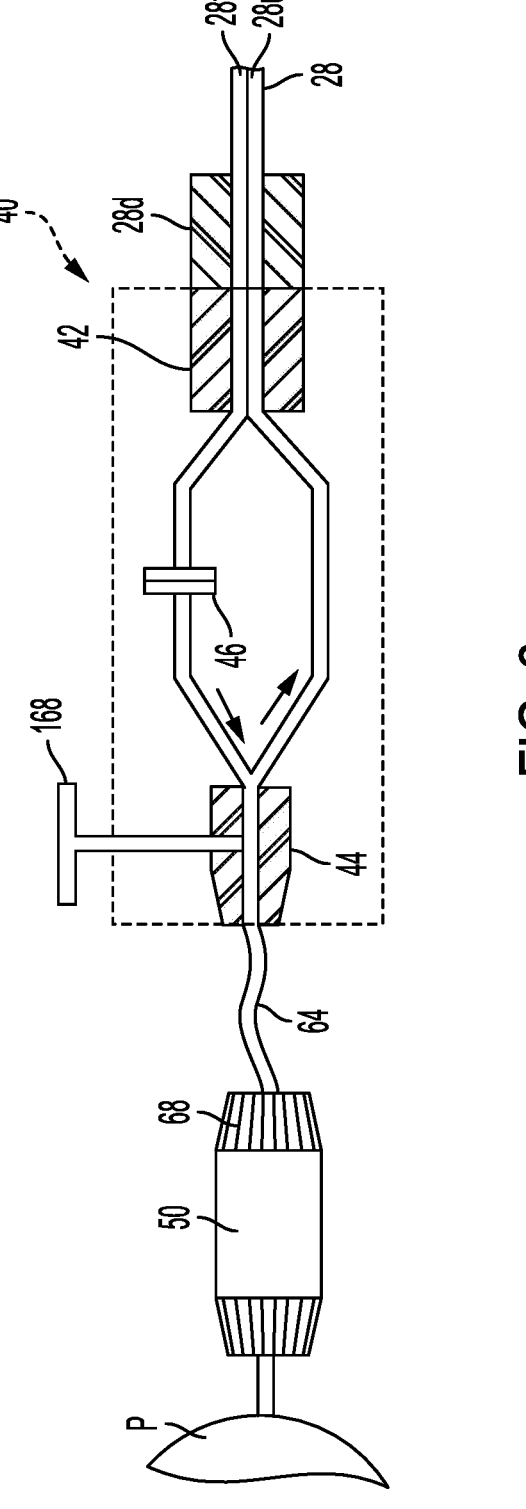
FIG. 2 is an elevation view of one embodiment for a valved patient transfer set or a valved disposable filter set of the present disclosure.

Disposable filter set 40 and a transfer set 50 for patient P are illustrated in more detail in FIG. 2. FIG. 2 illustrates that dual lumen patient line 28 includes a fresh PD fluid lumen 28f and a used PD fluid lumen 28u. Fresh PD lumen 28f carries fresh PD fluid from PD machine 20 to and through sterilizing grade filter membrane 46 of disposable filter set 40. Used PD fluid lumen 28u carries used PD fluid from the used PD fluid side of disposable filter set 40 to PD machine 20. FIG. 2 further illustrates that a short flexible line 64 is located between disposable filter set 40 and patient P's transfer set 50. Short flexible line 64 breaks up the generally rigid disposable filter set 40 and patient transfer set 50 so they do not have to be connected together to form a large generally rigid assembly that could become uncomfortable for the patient.

It is expected that fresh PD fluid lumen 28f will have an internal volume of around 30 to 50 ml, such as 35 ml. That volume of fluid resides within fresh PD fluid lumen 28f over the course of a patient dwell, e.g. for one to two hours, and therefore cools from a treatment temperature to room temperature. For a PD patient having a typical fill volume of one to two liters, initially receiving 30 to 50 ml of unheated, room temperature PD fluid is not a cause for concern as the patient is quickly filled with heated fresh PD fluid at a high flowrate of 200 to 250 ml/min. But for low volume patients, such as pediatric or infant patients, the fill volume can be much smaller, e.g., 300 ml or less. Also, the fill flowrates for low volume patients are also lower, such as 150 ml/min or less, such that the unheated, room temperature initial fill from PD fluid lumen 28f has a considerably larger comparative effect. Also, because the fill flowrate is lower, it takes longer to receive heated fresh PD fluid to warm the initially filled unheated PD fluid. The structure and methodology of the present disclosure are provided accordingly.

FIGS. 1 and 2 illustrate that one or both of disposable filter set 40, e.g., at connector 44, and/or patient transfer set 50 is provided with a manual valve 68, 168 such as a manual ball, twist, gate or needle valve. Patient transfer set 50 is typically provided with a valve 68, such as twist valve, such that disposable filter set 40 would not need to provide manual valve 168. In any case, at the end of a patient drain, control unit 100 via user interface 108 in one embodiment prompts the patient or caregiver to close manual valve 68, 168. The patient drain may end when (i) PD machine 20 records that a prescribed amount of used PD fluid or effluent has been removed from the patient, (ii) upon control unit 100 determining a low patient drain flowrate indicating that the patient is empty or almost empty, or (iii) upon control unit 100 determining an increased patient drain pressure, again indicating that the patient is empty or almost empty. At the end of the patient drain as determined by any one or more of (i) to (iii), user interface 108 audibly, visually or audiovisually prompts the patient or caregiver to close manual valve 68, 168.

After the prompt to close manual valve 68, 168 is provided by user interface 108, the user interface may display a confirm button, which the patient or caregiver presses to confirm that manual valve 68, 168 has been closed. At the same time, or after the confirm button has been pressed, control unit 100 causes PD machine valves 94b and 54f to open towards patient P, and PD fluid pump 70 to run a pressure test by attempting to pump PD fluid, e.g., a small amount such as five milliliters ("ml"), towards patient P. If manual valve 68, 168 has been properly closed, pressure sensor 78a outputting to control unit 100 will detect a quick rise in positive pressure of the closed line. If manual valve 68, 168 has not been properly closed, pressure sensor 78a will not detect the characteristic quick rise in positive pressure, wherein control unit 100 will then cause user interface 108 to audibly, visually or audiovisually prompt the patient or caregiver to close manual valve 68, 168. The above procedure is repeated until control unit 100 confirms that manual valve 68, 168 has been closed.

Once it is confirmed that manual valve 68, 168 has been closed, control unit 100 causes PD machine valves 94b and 54f to open towards patient P and PD machine valves 54r3 and 54r2 to open towards disposable drain line 36. Control unit 100 causes PD fluid pump 70 to pump at least a fresh PD fluid lumen volume's worth of fresh, heated PD fluid (e.g., 30 to 50 ml) along patient tubing or line 52f within PD machine 20 and into fresh PD fluid lumen 28f of reusable dual lumen patient line 28. A corresponding volume of unheated, room temperature PD fluid is displaced from fresh PD fluid lumen 28f into used PD fluid lumen 28u via disposable filter set 40. A similar corresponding volume of unheated, room temperature used PD fluid or effluent is displaced from used PD fluid lumen 28u, into lines or tubes 52g and 52r2 located within PD machine 20, pushing the used PD fluid towards drain line 36.

After the fresh PD fluid lumen volume's worth of fresh, heated PD fluid (e.g., 30 to 50 ml) is pumped by PD fluid pump 70 so as to fill fresh PD fluid lumen 28f, control unit 100 via user interface 108 prompts the patient or caregiver to open manual valve 68, 168 located either at the patient's transfer set 50 or at connector 44 of disposable filter set 40. After the prompt to close manual valve 68, 168 provided by user interface 108, the user interface may again display a confirm button, which the patient or caregiver presses to confirm that manual valve 68, 168 has been opened. After the confirm button has been pressed, control unit 100 causes PD machine valves 94b and 54f to open towards patient P, and PD fluid pump 70 to pump the patient's prescribed fill volume of fresh, heated PD fluid into the peritoneal cavity of patient P. The above process is repeated for each low volume patient fill.

The closing and opening of manual valve 68, 168 for each patient fill requires effort from the patient or caregiver over the course of treatment. It should be appreciated however that low volume patient fills do not occur frequently. It is accordingly contemplated to program control unit 100 such that upon receiving a device prescription for treatment, e.g., from one or more memory 104, an external memory such as a Universal Serial Bus ("USB") drive, or from a remote server, the control unit reviews the prescribed fill volume specified in the device prescription. If the prescribed patient fill volume is not a low volume patient fill, control unit 100 proceeds with a typical treatment in which the patient or caregiver is not prompted to close and open manual valve 68, 168 prior to each patient fill. If the prescribed patient fill volume is a low volume patient fill, e.g., 300 ml or less, control unit 100 enters a low fill volume mode in which the patient or caregiver is prompted to close and open manual valve 68, 168 prior to each patient fill as described herein.

PD treatments with typical patient fill volumes occur mostly in the patient's home and at night while the patient sleeps. As discussed herein, many low volume fills occur with pediatric patients who are not chronic kidney failure patients but instead have acute kidney failure as a result of some other illness or event, such as an accident. Here, the pediatric patient is treated in a hospital, e.g., in an intensive care unit, where a nurse is present to operate PD machine 20. The closing and opening of manual valve 68, 168 is performed by the nurse as one of the steps needed to treat the pediatric patient's acute kidney failure. It is further contemplated for control unit 100 to allow the low volume mode to be overridden at the time of treatment or be disabled for all treatments in a situation, for example, where a chronic kidney failure patient is small enough that their fill volume is a low fill volume. The patient may then choose to live with the filling of unheated PD fluid rather than having to manipulate manual valve 68, 168 as discussed herein.

Figure 3:
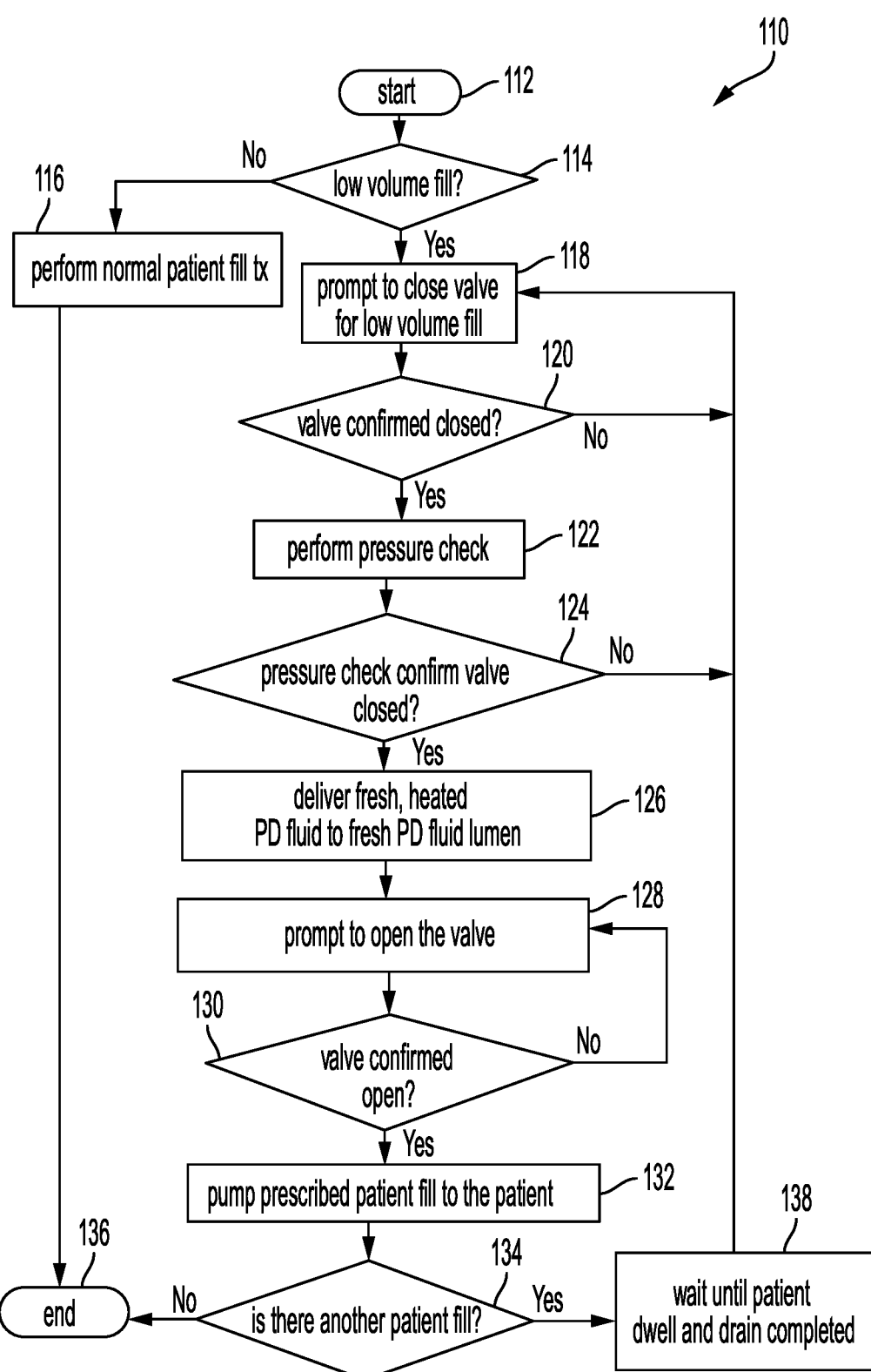
FIG. 3 is a process flow diagram illustrating one embodiment for operating the low volume patient fill of the present disclosure.

Method 110 of FIG. 3 summarizes the programing and operation of control unit 100. At oval 112, the method 110 begins. At diamond 114, control unit 100 determines if the prescribed patient fill volume is a low volume patient fill volume, e.g., is 300 ml or less. When the prescribed patient fill is not a low volume patient fill as determined at diamond 114, then at block 116 control unit 100 causes the PD treatment to be performed in a normal manner without flushing fresh PD fluid lumen 28f of unheated PD fluid. When the prescribed patient fill is a low volume patient fill as determined at diamond 114, then at block 118, control unit 100 causes user interface 108 to prompt the patient or caregiver to close manual valve 68, 168 and to confirm such closing.

At diamond 120, control unit 100 determines whether or not the patient or caregiver has confirmed the closing of manual valve 68, 168. If not, method 110 returns to block 118 and continues to prompt the patient or caregiver to close manual valve 68, 168 and to confirm such closing. When the patient or caregiver has confirmed the closing of manual valve 68, 168, as determined at diamond 120, control unit 100 at block 122 causes a pressure check to be performed in the manner described herein to ensure that manual valve 68, 168 has been fully closed. In an alternative embodiment, control unit 100 runs pressure checks periodically after prompting the patient or caregiver to close manual valve 68, 168 at block 118.

At diamond 124, control unit 100 determines whether or not the pressure check confirms that manual valve 68, 168 has been properly closed. If not, method 110 again returns to block 118 and continues to prompt the patient or caregiver to close manual valve 68, 168 and to confirm such closing. When the pressure check confirms that manual valve 68, 168 has been properly closed, as determined at diamond 124, control unit 100 at block 126 causes PD fluid pump 70 with the appropriate PD machine valves open to pump at least an internal fresh fluid lumen volume's worth of fresh, heated PD fluid into fresh PD fluid lumen 28f, expelling the unheated PD fluid through disposable filter set 40 into used PD fluid lumen 28u as discussed herein.

After heated PD fluid is delivered into fresh PD fluid lumen 28f at block 126, control unit 100 at block 128 causes user interface 108 to prompt the patient or caregiver to open manual valve 68, 168 and to confirm such opening. At diamond 130, control unit 100 determines whether or not the patient or caregiver has confirmed the opening of manual valve 68, 168. If not, method 110 returns to block 128 and continues to prompt the patient or caregiver to open manual valve 68, 168 and to confirm such closing. If the patient or caregiver has confirmed the opening of manual valve 68, 168, as determined at diamond 130, control unit 100 at block 132 causes PD fluid pump 70 with the appropriate valves open to pump a prescribed low fill volume of fresh, heated PD fluid into the peritoneal cavity of the patient.

In an alternative and in one preferred embodiment for diamond 130, control unit 100 confirms the opening of valve 68, 168 via a pressure test instead of via a user confirmation. The pressure test may be performed by causing PD fluid pump 70 to pump a small amount of fluid, such as five milliliters ("ml"), towards the patient at valve 68, 168. If manual valve 68, 168 has been properly opened, the relevant pressure sensor, e.g., pressure sensor 78a, will not see a significant pressure rise, after which the patient's prescribed fill volume of fresh, heated PD fluid at block 132 is pumped into the peritoneal cavity of the patient. In a further alternative embodiment for diamond 130, control unit 100 confirms the opening of valve 68, 168 via a pressure test in which PD fluid pump 70 applies a small amount of pressure, positive or negative (e.g., 6.9 kPa (1 psig) or −6.9 kPa (−1 psig)), at the patient valve 68, 168, before instructing the user to open the valve. When the manual valve 68, 168 has been properly opened, the relevant pressure sensor, e.g., pressure sensor 78a, will see a significant pressure increase or decrease, after which the patient's prescribed fill volume of fresh, heated PD fluid at block 132 is pumped into the peritoneal cavity of the patient.

At diamond 134, control unit 100 determines whether or not there is another prescribed patient fill remaining in the current treatment. If not, method 110 ends at oval 136. If there is another prescribed patient fill remaining in the current treatment, as determined at diamond 134, then control unit 110 at block 138 waits for the subsequent patient dwell to end and the subsequent drain to be performed, and then returns to block 118 to prompt the patient or caregiver to close manual valve 68, 168 for the next low volume patient fill.

It should be understood that various changes and modifications to the presently preferred embodiments described herein will be apparent to those skilled in the art. It is therefore intended that such changes and modifications be covered by the appended claims. For example, system 10 does not have to use redundant or durable components, does not have to employ disinfection, such as heat disinfection, and may instead employ a disposable set having a disposable pumping portion that contacts the corresponding medical fluid. Such disposable cassette may employ dual lumen reusable patient line 28 and may or may not employ disposable filter set 40. While disposable filter set 40 would not be needed as a last chance filter for a system not using heat disinfection, disposable filter set 40 may still be provide if the fresh PD fluid is made online at the time of use as a last chance filter for the online PD fluid. PD fluid pumping with the disposable set may be performed alternatively via pneumatic pump actuation of a sheet of a disposable cassette of the disposable set, via electromechanical pump actuation of a sheet of a disposable cassette of the disposable set, or via peristaltic pump actuation of a pumping tube segment provided with the disposable set.

Further alternatively, while valve 68, 168 is described as being a manual valve, valve 68, 168 may alternatively be an electrically or pneumatically controlled valve under control of control unit 100. Here, control unit 100 may perform the steps of method 110 automatically at the end of a drain and not require patient or caregiver manual action or confirmation.

Still further alternatively, while system 10 and associated methodology have been described using dual lumen patient line 28, a single lumen patient line could be used instead. Here, the goal is not to replace cold PD fluid because the single lumen patient line is instead filled with heated used PD fluid or effluent from the previous drain. Instead, the goal is to remove the used PD fluid so it is not returned to the low volume patient where it may make up a relatively large portion of the prescribed patient fill. Here, disposable filter set 40 or the transfer set 50 for the patient may be provided with a hydrophobic membrane, which allows air to aseptically backfill the used PD fluid, which is removed via PD machine 20 from the single lumen patient line to drain while valve 68, 168 is closed. With valve 68, 168 still closed, control unit 100 causes fresh, heated PD fluid to be pumped into the single lumen patient line, pushing the aseptic air to atmosphere through the hydrophobic membrane. When all the air has been removed to atmosphere, and the patient line is filled with fresh, heated PD fluid, control unit 100 senses a pressure spike at pressure sensor 72a, at which point the single lumen patient line filling is stopped. Valve 68, 168 may then be opened to perform the prescribed patient fill using only fresh, heated PD fluid.

The invention is claimed as follows:

1. A peritoneal dialysis ("PD") system comprising:
a housing;
a PD fluid pump housed by the housing;
a dual lumen patient line extending from the housing, the dual lumen patient line including a fresh PD fluid lumen and a used PD fluid lumen;
a filter set in fluid communication with the fresh PD fluid lumen and the used PD fluid lumen of the dual lumen patient line;
a valve provided either with a patient's transfer set or with the filter set, the valve positioned such that when closed, PD fluid is forced from the fresh PD fluid lumen into the used PD fluid lumen; and
a control unit configured to control the PD fluid pump, the control unit further configured after a patient drain to:
  (i) prompt a patient or caregiver to close the valve when the valve is a manual valve, or
  (ii) cause the valve to close automatically when the valve is an electrically or pneumatically controlled valve,
wherein the control unit is further configured after the closing of the valve to cause the PD fluid pump to pump fresh, heated PD fluid into the fresh PD fluid lumen to displace unheated PD fluid from the fresh PD fluid lumen, through the filter set, into the used PD fluid lumen.

2. The PD system of claim 1, wherein the filter set includes a sterilizing grade filter membrane, and wherein the displaced unheated PD fluid is displaced through the sterilizing grade filter membrane into the used PD fluid lumen.

3. The PD system of claim 1, wherein the manual valve is a manual ball, twist, gate, or needle valve.

4. The PD system of claim 1, further including a pressure sensor, wherein the control unit is further configured to cause the PD fluid pump to attempt to pump a test amount of fresh PD fluid towards the fresh PD fluid lumen, and to monitor an output from the pressure sensor to determine if the valve is closed.

5. The PD system of claim 4, wherein the control unit is further configured to monitor the output from the pressure sensor to determine if the valve is closed prior to causing the PD fluid pump to pump fresh, heated PD fluid into the fresh PD fluid lumen to displace unheated PD fluid from the fresh PD fluid lumen, through the filter set, into the used PD fluid lumen.

6. The PD system of claim 4, wherein the control unit is further configured to monitor the output from the pressure sensor after the patient or caregiver confirms that the manual valve has been closed.

7. The PD system of claim 1, wherein prompting the patient or caregiver to close the valve, when the valve is the manual valve, includes providing a confirm button for the patient or caregiver to press after closing the manual valve.

8. The PD system of claim 1, wherein the control unit is further configured, after the PD fluid pump is caused to pump fresh, heated PD fluid into the fresh PD fluid lumen, to:
  (iii) prompt the patient or caregiver to open the valve when the valve is the manual valve, or
  (iv) cause the valve to be opened automatically when the valve is the electrically or pneumatically controlled valve.

9. The PD system of claim 8, wherein prompting the patient or caregiver to open the valve when the valve is the manual valve includes providing a confirm button for the patient or caregiver to press after opening the manual valve.

10. The PD system of claim 8, wherein the control unit is further configured to cause the PD fluid pump to pump a prescribed fill volume of fresh, heated PD fluid to the patient after the valve is opened.

11. A peritoneal dialysis ("PD") system comprising:
a housing;
a PD fluid pump housed by the housing;
a dual lumen patient line extending from the housing, the dual lumen patient line including a fresh PD fluid lumen and a used PD fluid lumen;
a valve provided with a patient's transfer set, the valve positioned such that when closed, PD fluid is forced from the fresh PD fluid lumen into the used PD fluid lumen; and
a control unit configured to control the PD fluid pump, the control unit further configured after a patient drain to:
  (i) prompt a patient or caregiver to close the valve when the valve is a manual valve, or
  (ii) cause the valve to close automatically when the valve is an electrically or pneumatically controlled valve,
wherein the control unit is further configured after the closing of the valve to cause the PD fluid pump to pump fresh, heated PD fluid into the fresh PD fluid lumen to displace unheated PD fluid from the fresh PD fluid lumen into the used PD fluid lumen.

12. A peritoneal dialysis ("PD") system comprising:
a housing;
a PD fluid pump housed by the housing;
a patient line extending from the housing;
a filter set in fluid communication with the patient line;
a valve provided either with a patient's transfer set or with the filter set, the valve positioned such that when closed, PD fluid is removed from the patient line; and
a control unit configured to control the PD fluid pump, the control unit further configured after a patient drain to:
  (i) prompt a patient or caregiver to close the valve when the valve is a manual valve, or
  (ii) cause the valve to close automatically when the valve is an electrically or pneumatically controlled valve,
wherein the control unit is further configured after the closing of the valve to cause the PD fluid pump to pump fresh, heated PD fluid into the patient line.

13. The PD system of claim 12, wherein PD fluid is removed from the patient line to drain and is backfilled with filtered air.

14. A peritoneal dialysis ("PD") system comprising:
a housing;
a PD fluid pump housed by the housing;
a patient line extending from the housing;
a valve provided with a patient's transfer set, the valve positioned such that when closed, PD fluid is removed from the patient line; and
a control unit configured to control the PD fluid pump, the control unit further configured after a patient drain to:
  (i) prompt a patient or caregiver to close the valve when the valve is a manual valve, or
  (ii) cause the valve to close automatically when the valve is an electrically or pneumatically controlled valve,
wherein the control unit is further configured after the closing of the valve to cause the PD fluid pump to pump fresh, heated PD fluid into the patient line.

15. The PD system of claim 14, wherein PD fluid is removed from the patient line to drain and is backfilled with filtered air.

*  *  *  *  *